(12) United States Patent
Lu

(10) Patent No.: US 9,994,519 B2
(45) Date of Patent: Jun. 12, 2018

(54) SYNTHETIC ANTIOXIDANTS AND THEIR USES

(71) Applicant: Yansong Lu, Edison, NJ (US)

(72) Inventor: Yansong Lu, Edison, NJ (US)

(*) Notice: Subject to any disclaimer, the term of this patent is extended or adjusted under 35 U.S.C. 154(b) by 158 days.

(21) Appl. No.: 14/647,260

(22) PCT Filed: Apr. 18, 2013

(86) PCT No.: PCT/US2013/037038
§ 371 (c)(1),
(2) Date: May 26, 2015

(87) PCT Pub. No.: WO2014/084898
PCT Pub. Date: Jun. 5, 2014

(65) Prior Publication Data
US 2015/0336884 A1    Nov. 26, 2015

Related U.S. Application Data

(60) Provisional application No. 61/730,508, filed on Nov. 28, 2012.

(51) Int. Cl.
| | | |
|---|---|---|
| C07D 487/04 | (2006.01) | |
| C07C 327/06 | (2006.01) | |
| C07C 327/48 | (2006.01) | |
| C07C 327/26 | (2006.01) | |
| C07D 213/83 | (2006.01) | |
| C07D 213/65 | (2006.01) | |
| C07D 241/24 | (2006.01) | |
| C07D 239/38 | (2006.01) | |
| C07C 321/26 | (2006.01) | |
| C07C 327/18 | (2006.01) | |

(52) U.S. Cl.
CPC .......... *C07C 327/06* (2013.01); *C07C 321/26* (2013.01); *C07C 327/18* (2013.01); *C07C 327/26* (2013.01); *C07C 327/48* (2013.01); *C07D 213/65* (2013.01); *C07D 213/83* (2013.01); *C07D 239/38* (2013.01); *C07D 241/24* (2013.01); *C07D 487/04* (2013.01)

(58) Field of Classification Search
CPC .. C07D 213/65; C07D 213/83; C07D 239/38; C07D 241/24; C07D 487/04; C07C 321/26; C07C 327/06; C07C 327/18; C07C 327/26; C07C 327/48
See application file for complete search history.

(56) References Cited

U.S. PATENT DOCUMENTS

5,698,580 A * 12/1997 Kajiyashiki .......... C07D 339/08
514/436

FOREIGN PATENT DOCUMENTS

| | | |
|---|---|---|
| CN | 1678592 A | 10/2005 |
| EP | 0225471 A1 | 6/1987 |
| EP | 0348166 A2 | 12/1989 |
| EP | 1300428 A2 | 4/2003 |
| GB | 858482 A | 1/1961 |
| IE | 20060312 A1 | 12/2007 |
| JP | S61266458 A | 11/1986 |
| WO | 0031060 A1 | 6/2000 |

OTHER PUBLICATIONS

Hinsberg, Behavior of Aromatic Disulphides at High Temperatures, Freiburg i/Br. Ber., 43, 1874-9 (1910).*
Hinsberg et al., "Behavior of Aromatic Disulphides at High Temperatures," 43:1874-1879 (Chemical Abstract.
Miyahara et al., "Antitumor Effect of Compounds Synthesized in the Division of Synthetic Chemistry VI," 100:163-165.
Tanaka et al., "Studies on Sulfur-contaiing chelating agents. IX. Syntheses of Alkyl or Arl o-Mercaptophenyl Ketones, Esters of o-Mercaptothiobenzoic Acid, and their metal Chelates," Chemical and Pharmaceutical Bulletin (1962); 10:25-31.

* cited by examiner

*Primary Examiner* — Erich A Leeser
(74) *Attorney, Agent, or Firm* — Fox Rothschild LLP

(57) ABSTRACT

The present invention relates to synthetic organic antioxidants of small molecules. The novel dithiol-containing compounds in this invention possess strongest possible capability as both scavenger for free radicals and antioxidant. This invention is directed to novel molecules as prodrugs of the novel dithiol-containing compounds, their rational design, their feasible preparation route by means of synthetic organic chemistry, and their potential uses in application to treatment and/or prevention of major diseases associated with oxidative stress, such as Alzheimer's disease, Parkinson's disease, cancer, diabetes, HIV, acne, cardiovascular disease, renal disease, hypertension, hypercholesterolemia, hyperlipidemia, rheumatoid arthritis, inflammation, pain, aging, stroke, cataract, glaucoma, age-related macular degeneration, etc.

10 Claims, 4 Drawing Sheets

SYNTHETIC ANTIOXIDANTS AND THEIR USES

CROSS REFERENCE TO RELATED APPLICATIONS

The present application is the 35 U.S.C. § 371 National Phase Application of International Application Ser. No. PCT/US2013/037038, filed on Apr. 18, 2013, which in turn claims benefit of priority to U.S. Provisional Application Ser. No. 61/730,508 filed on Nov. 28, 2012, the entire contents of which are herein incorporated by reference.

FIELD OF THE INVENTION

This invention relates to novel synthetic organic antioxidants of small molecules, their rational design, their proposed chemical preparation, and their potential uses in application to treatment and/or prevention of major diseases associated with oxidative stress.

BACKGROUND OF THE INVENTION

There is a delicate-regulated redox system in living organism. In a healthy human body, any harmful oxidants, whether from endogenous or exogenous origin, are efficiently neutralized by corresponding reductases in a timely manner so as to protect important biological macromolecules such as proteins, DNA and lipids, from being oxidized. However, under unbalanced conditions when there are more amounts of harmful oxidants than the capacity of reductases to deal with, which is called the state of oxidative stress, excessive oxidants can oxidize important biological macromolecules such as proteins, DNA and lipids, leading to malfunction or dysfunction of these important biological macromolecules and resulting in serous illness or even death. These harmful oxidants are basically reactive oxygen species (ROS) and reactive nitrogen species (RNS). Among them, the majority are free radicals.

There are three sources of free radicals for a human body. Internal source includes mitochondria, inflammation, exercise, xanthine oxidase, peroxisomes, phagocytes, etc. Free radicals from internal source are actually generated from normal metabolic cycles. Part of them is used by immune system to fight against the invasion of bacteria or virus. Their functions also include redox signaling, cleaning up death cells, activating and modulating some important life processes, etc. Overall, free radicals from internal source are often kept under control by the redox system. External source includes cigarette smoke, alcoholism, toxins, certain drugs, ozone, UV light, radiation, pesticides, herbicides, environmental pollutants, etc. The third source is related to physiological factors, including stress, emotion, disease conditions, etc. Free radicals from the latter two sources are usually extra burdens of the redox system and they are the roots of oxidative stress that causes health problems.

Free radicals have been implicated in the etiology of large number of major diseases, such as Alzheimer's disease, Parkinson's disease, cancers, diabetes, HIV, acne, cardiovascular disease, renal disease, hypertension, hypercholesterolemia, hyperlipidemia, rheumatoid arthritis, inflammation, pain, aging, stroke, cataract, glaucoma, age-related macular degeneration, etc. Antioxidants that can combat free radicals have drawn significant attention in past decades. Natural sources of antioxidants include fruits, vegetables and other dietary. Herbal polyphenols, flavonoids, beta-carotene, vitamin A, vitamin C, vitamin E, lipoic acid, dithiolethione, ovothiol, glutathione and melatonin are some examples of naturally occurring antioxidants. However, some problems might be encountered when naturally occurring antioxidants are directly used as drugs. Their bioavailability may not be good enough because many of them have poor solubility in water. Their antioxidant power may not precisely fit in the indication. Some polyphenols can form precipitates with proteins (enzymes) down the digestive tract, resulting in poor bioavailability and causing digestion issue.

There has been much less number of synthetic organic antioxidants so far than that of natural occurring antioxidants. Edaravone, pirenoxine, phacolin and bendazac are some examples of synthetic organic antioxidants. These four are not approved by FDA for use as drugs in US. But they are approved for use as drugs in some other countries, even though none of them has remarkable therapeutic effects nor is a drug for major diseases. BHT(2,6-Di-tert-butyl-4-methylphenol) is another example of synthetic organic antioxidant, which is widely used gas a stabilizer for storage of some organic solvents, such as THF and diethyl ether, etc., to protect them from being air-oxidized. Oltipraz, DTT (dithiothreitol), probucol and succinobucol are other examples of synthetic organic antioxidants. None of these has been approved as antioxidant drug, although oltipraz is used as a schistosomicide. But the advantages of synthetic organic antioxidants are clear that they can be designed in such a way to enhance the bioavailability, to minimize their toxicities, to tune in the scavenging power on free radicals, and so forth. Synthetic antioxidants can certainly play an important role in treatment and/or prevention of major diseases that pare associated with oxidative stress.

By definition, antioxidants are a class of compounds that can deactivate reactive oxidants by means of being oxidized themselves. As of being readily oxidized, the organic antioxidants are often aniline-like compounds (including indole-like), phenol or polyphenol compounds, thiol-containing compounds and selenol-containing compounds. In order to be used as drugs, both reduced form and oxidized form of the ideal antioxidant should not have any toxicity issues. For example, phosphine compounds are known to be easily oxidized and can be good antioxidants in chemical wise. But they are ruled out as drugs due to toxicity issues.

The theory of free radicals and antioxidants related to human health is widely accepted in main stream of science worldwide. Numerous research papers have been published in large scope of scientific journals and this trend is still continuing. Positive results are reported from many vitro and vivo tests, and even reported from some early phase clinical trials. Since 1990's, however, several strictly designed clinical trials have shown inconclusive results, no efficacy or high adverse effects on high dose of several antioxidants, casting shadows on this research area. A breakthrough is urgently needed.

PRIOR ART

1. Current Situation of Natural Antioxidants and Synthetic Antioxidants

As a summary in chemistry theory, a drug-to-be molecule of organic antioxidant should first be a nitrogen-containing, oxygen-containing, sulfur-containing, or selenium-containing compound. A nitrogen-containing molecule is usually aniline-like (including indole-like) because aniline is more readily oxidized than amine. Edaravone, pirenoxine, phacolin, melatonin and bendazac are examples of aniline-like antioxidant compounds. While other four are chemically synthesized, melatonin is found in human body, secreted by pineal gland. Melatonin is also well known for its hormone functions.

Some Reported Aniline-Like Antioxidants

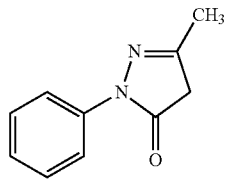

Edaravone

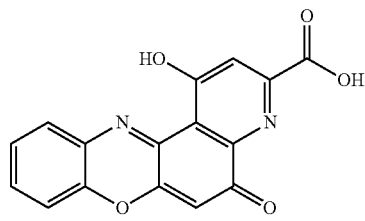

Pirenoxine

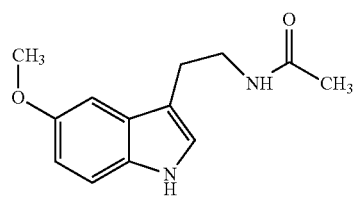

Melatonin

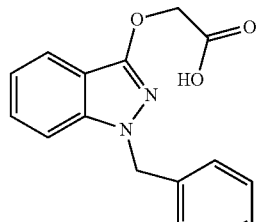

Bendazac

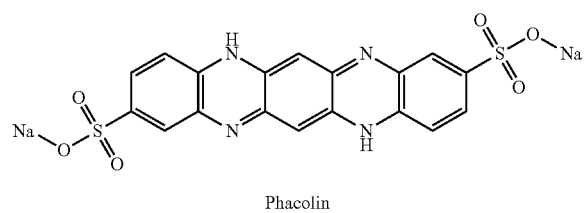

Phacolin

An oxygen-containing antioxidant is usually phenol-like because phenol is more readily oxidized than alkyl alcohol. Luteolin, resveratrol, vitamin C and vitamin E are examples of phenolic antioxidant compounds. These are naturally occurring antioxidants Some Reported Phenol-Like Antioxidants

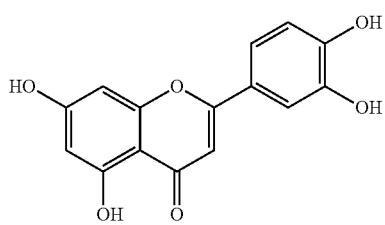

Luteolin

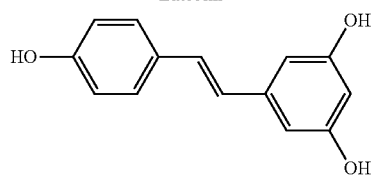

Resveratrol

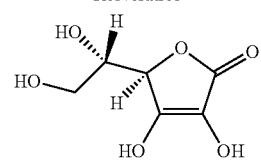

Vitamin C

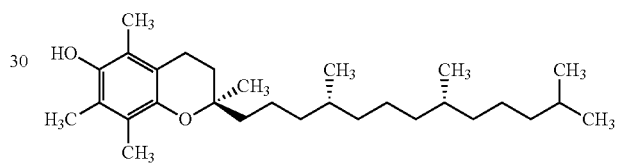

Alpha-Tocopherol (α-vitamin E)

An interesting example of synthetic phenolic antioxidant is succinobucol (AGI-1067) of AtheroGenics, which is similar to BHT in structure. AGI-1067 was an investigational drug for indications of type II diabetes, inflammation and cardiovascular disease. But it showed no efficacy in phase III clinical trial in 2008.

Two Examples Of Synthetic Phenol-Like Antioxidants

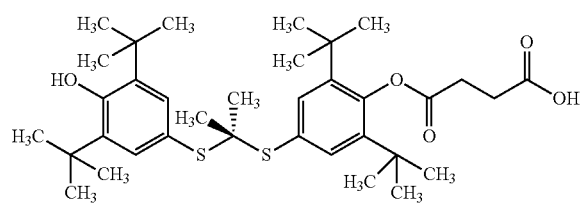

AGI-1067

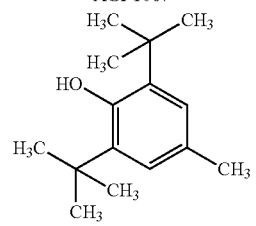

BHT

Another example of phenol-like antioxidant compounds is leonurine, which is originally isolated from extracts of herbal and now can be synthesized. Leonurine is reported to reduce arterial plaque and fibrosis on rabbits. But there is no report whether or not it has been in clinical trials.

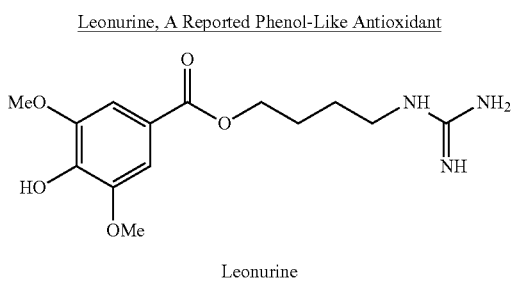 [SMILES: COc1cc(C(=O)OCCCCNC(=N)N)cc(OC)c1O]

Leonurine, A Reported Phenol-Like Antioxidant

Leonurine

Aspirin is perhaps the most popular drug in the world. It has been widely used as anti-inflammation, pain-killer, fever-reducer, blood-thinner, preventing stroke and heart attack, etc. Expanded applications of aspirin in treatment and/or prevention of cancers, Alzheimer's disease and diabetes are under wide studies in recent years. In vivo, aspirin turns into salicylic acid, which is a phenolic antioxidant. Thus, aspirin can be considered as a prodrug of antioxidant. NOSH-aspirin, called super aspirin, is a derivative of aspirin. It contains nitric oxide-releasing group and hydrogen sulfide-releasing group. NOSH-aspirin is reported to prevent cancer, anti-inflammation, and prevent heart attack, in pre-clinical study.

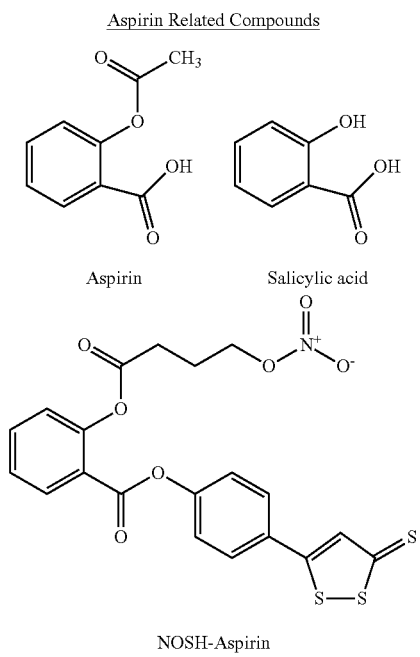

Aspirin Related Compounds

Aspirin    Salicylic acid

NOSH-Aspirin

Cysteine is a sulfur-containing, naturally occurring amino acid, well known for its function in biological redox system. Its oxidized form, cystine, plays an important role in advanced structure/configuration of proteins (enzymes). Glutathione and ovothiol are thiol-containing antioxidant compounds. Glutathione is found involved in the enzyme-catalytic-cycle of redox system in all tissue and organs. In healthy cells and tissue, the ratio of the disulfide form (GSSG) to the reduced form (GSH) is less than 1/9. An increased GSSG-to-GSH ratio is considered indicative of oxidative stress.

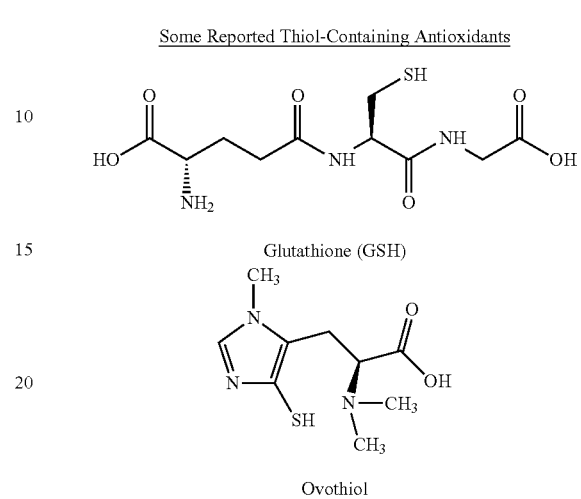

Some Reported Thiol-Containing Antioxidants

Glutathione (GSH)

Ovothiol

Lipoic acid, DTT (dithiothreitol) and oltipraz are dithiol-containing antioxidant compounds. When a dithiol-containing compound can form 5 or 6-membered ring via disulfide bond, it is a much stronger free radical scavenger than a corresponding mono thiol-containing compound. Lipoic acid is found in disulfide form (oxidized form), because the reduced form is relatively unstable and prone to air-oxidation. Many efforts have been applied to synthesize various derivatives of lipoic acid (US patent App. No. 20020048798; U.S. Pat. No. 6,900,338; US patent App. No. 20100317608), Dithiolane compounds (WO2010040603) and dithiolethione compounds (US patent App. No. 20060194971) were also published.

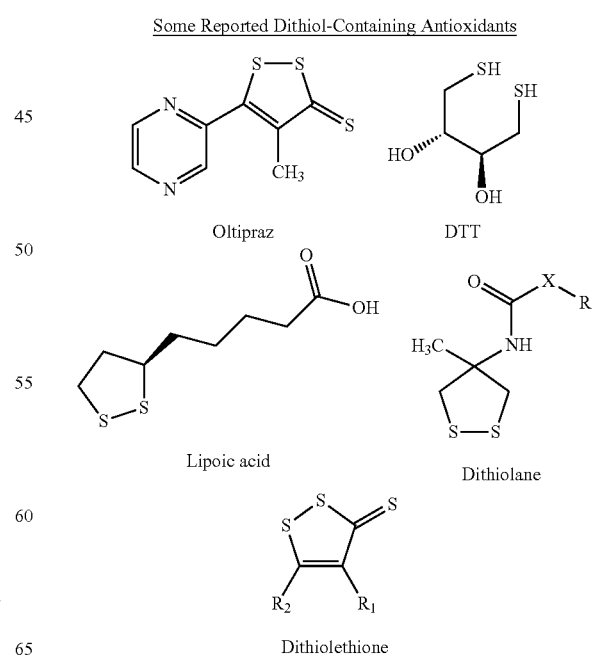

Some Reported Dithiol-Containing Antioxidants

Oltipraz        DTT

Lipoic acid        Dithiolane

Dithiolethione

DTT (dithiothreitol) is commonly used as a reagent to break disulfide bond of a substrate, by forming a 6-membered ring itself via a new disulfide bond (W. W. Cleland, *Biochemistry*, v. 3, 480, 1964). Obviously, the driving force is the cyclization itself via forming a new disulfide bond. However, neither DTT nor DTE (dithioerythritol) has been used as a drug due to toxicity issue.

It is worth mentioning that some interesting molecules were reported (Garner, et al., US patent App. No. 20090192212). Sulfur atom is placed at allylic position, where the sulfur atom is activated and it helps form disulfide.

Some Reported Dithiol-Containing Antioxidants

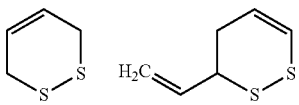

2. Clinical Trial Situation of Antioxidants as Investigational Drugs

Numerous studies in clinical trials have been carried out on many naturally occurring antioxidants, such as vitamin A, vitamin C, vitamin E, melatonin, beta-carotene, in treatment or prevention of a variety of diseases, such as neurodegenerative diseases, cancer, inflammation, atherosclerosis, aging, etc. No efficacy, marginal benefits or controversial results have been obtained. In some studies, vitamin A, vitamin E, and beta-carotene even leads to higher adverse effects, such as higher mortality or higher risk of certain cancers.

Synthetic antioxidants, which are not fully explored yet, are drawing more attention nowadays. Therefore, more powerful antioxidants and free radical scavengers are critically needed. Besides, other issues such as choosing appropriate biomarkers and selecting appropriate animal models for efficacy should be carefully addressed. Delicate design on drug penetration can better enhance the bioavailability of investigational drugs and thus plays important role in this invention. Since there is no antioxidant drug for major diseases being marketed with remarkable therapeutic effect, nor approved by FDA yet, this invention presents novel, drug-to-be molecules designed with the strongest possible power of antioxidant and of scavenger for free radicals, with reasonable bioavailability and with no toxicity issue hopefully as this has to be further tested.

SUMMARY OF THE INVENTION

This invention is directed to novel dithiol-containing compounds which possess strongest possible capability as both scavenger for free radicals and antioxidant, their rational design, their proposed preparations by means of synthetic organic chemistry, and their potential uses in application to treatment and/or prevention of major diseases associated with oxidative stress, such as Alzheimer's disease, Parkinson's disease, cancer, diabetes, HIV, acne, cardiovascular disease, renal disease, hypertension, hyperlipidemia, hypercholesterolemia, rheumatoid arthritis, inflammation, pain, aging, stroke, cataract, glaucoma, age-related macular degeneration, etc.

DESCRIPTION OF THE EMBODIMENTS OF THE INVENTION

Figure 1:
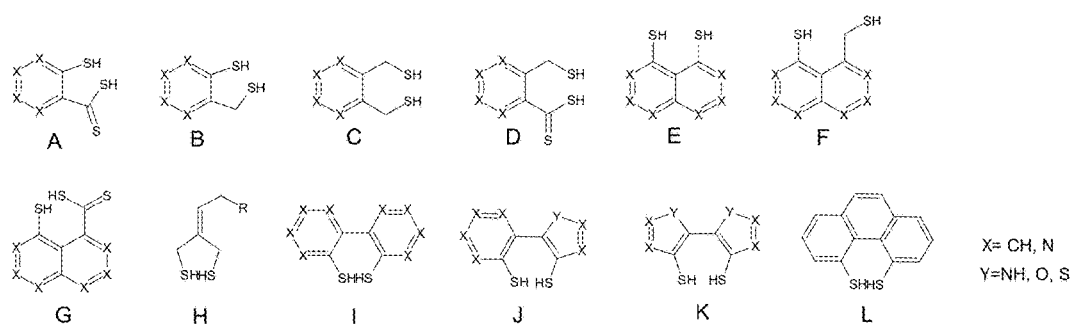
FIG. 1 illustrates some basic styles of novel dithiol-containing antioxidants.

1. Rational Design for Strongest Possible Antioxidants and Scavengers of Free Radicals In order to be used as an antioxidant, a compound must consist of at least one functional group that can be readily oxidized. From the periodic table of the elements, the functional group of a drug-to-be organic antioxidant must consist of at least an atom of low valent nitrogen, oxygen, sulfur, or selenium. The order of antioxidant strength is selenophenol>thiophenol>aniline>phenol, based on chemistry theory. In addition, the order of antioxidant strength is thiophenol>alkyl thiol; aniline>alkyl amine, and so forth.

The strength of a free radical scavenger is not identical to its strength as an antioxidant, even though they are relevant. Three features of free radical chemistry are initiation, propagation and termination. In initiation stage, free radical can be generated by heat, light, radiation, metabolic cycles or some certain chemical reagents. Free radical can propagate by means of electron transfer or hydrogen radical transfer. In propagation stage, the total number of free radicals is constant, with some disappeared and some emerged at the same time. Scheme I shows the propagation of free radical. Termination of free radicals can be done by reacting one free radical with another to form a coupling compound. In this stage, free radicals disappear. Scheme II shows the termination of two free radicals by forming a coupling compound.

Scheme I. Propagation of Free Radicals

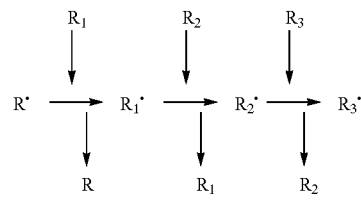

Reactivity: R˙ > R₁˙ > R₂˙ > R₃˙

Although the reactivity of each free radical in scheme I is diminishing down the track, they are still free radicals and each of them is still capable of taking in an electron or a hydrogen radical from other vulnerable molecules. Therefore, each of them is considered as pro-oxidant, as they can still oxidize other molecules by taking in electrons or hydrogen radicals. This is exactly what happened to vitamin E, vitamin A or beta-carotene when they were used in clinical trials to against some certain cancers. For example, when a molecule of vitamin E deactivates a harmful free radical, itself becomes a free radical as shown below. The free radical form of vitamin E is a pro-oxidant and is still capable of doing harm to important biological macromolecules such as proteins, DNA and lipids. This can well explain why higher rate of some certain cancers were observed when vitamin E, vitamin A or beta-carotene were used in clinical trials. These clinical trial data can, from another hand, verify that the hypothesis that free radicals can cause cancers by damaging DNA and/or other important biological macromolecules is true. Free radical scavengers as antioxidant drugs, therefore, are no doubt going to work. The key is how to efficiently terminate free radicals, so as to avoid the lengthy propagation of free radicals. This prompts innovative designs for novel drug molecules in this invention.

Free Radical Form Of Alpha-Tocopherol (α-Vitamin E)

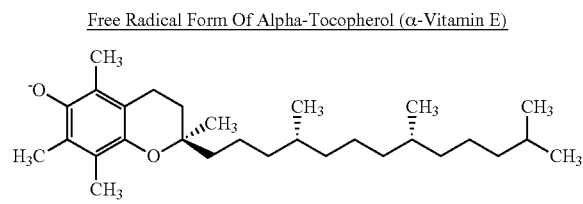

Scheme II.

Termination Of Free Radicals By Forming A Coupled Compound

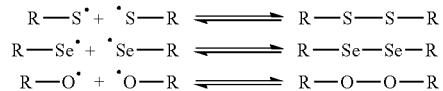

Bond Energy:

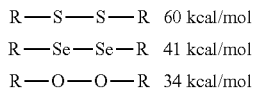

From scheme II, bond energy of peroxide is the lowest. This means that the reaction can readily go to the left side. Actually, peroxide can easily undergo homolytic cleavage generating two free radicals. Besides, bond energy of disulfide is higher than that of diselenide. It means that thiol is a more powerful scavenger of free radicals than selenol, although selenol is a stronger antioxidant than thiol. In addition, N—N single bond energy is 38 kcal/mol that is not shown in scheme II. Thus, disulfide has the highest bond energy among all interested functional groups and thiol is hence the most powerful scavenger of free radicals among them.

Scheme III. One Dithiol-Containing Molecule Nullifies Two Free Radicals

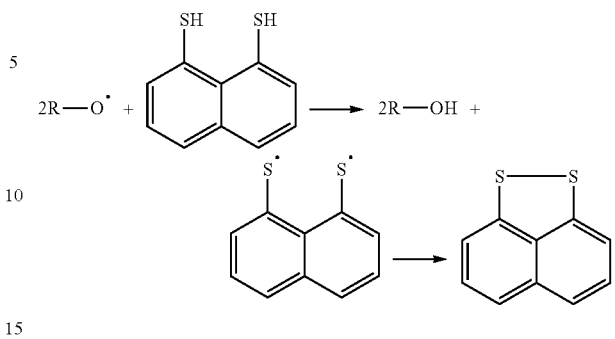

According to the theory of chemical kinetics, a dithiol-containing molecule (drug) has a much faster reaction rate than that of mono thiol-containing molecule, to form the disulfide yin scheme II, especially when it can form a 5-membered ring via a disulfide bond. Besides, one dithiol-containing molecule (drug) can efficiently terminate two free radicals as illustrated in scheme III.

Oxidative damage of protein by free radicals is mainly ascribed to the formation of cross-linking via disulfide bonds. The structural alteration caused by the cross-linking leads to dysfunction or malfunction of the protein. In addition, it is well known that thiol-disulfide exchange is reversible (scheme IV). Therefore, it is possible to use an appropriate thiol-containing reagent (drug) to convert disulfide of damaged protein back to thiols of normal protein and thus to fix the oxidative damage of the protein.

Scheme IV. Thiol-Disulfide Exchange

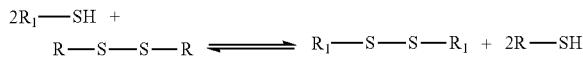

Based on chemical kinetics, a dithiol-containing molecule (drug) has maximum driving force to push the equilibrium to the right side in scheme IV. The driving force is clearly from the intramolecular cyclization of the dithiol-containing molecule via forming a disulfide bond. When cyclization via a disulfide bond occurs by free radical mechanism, it is favored to form a 5-membered ring. However, when cyclization occurs via non-free-radical mechanism, a 6-membered ring is favored. This is illustrated in scheme V.

Scheme V. A Novel Drug Could Reverse A Damaged Protein

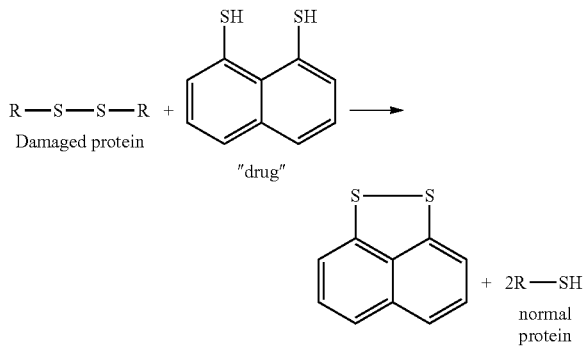

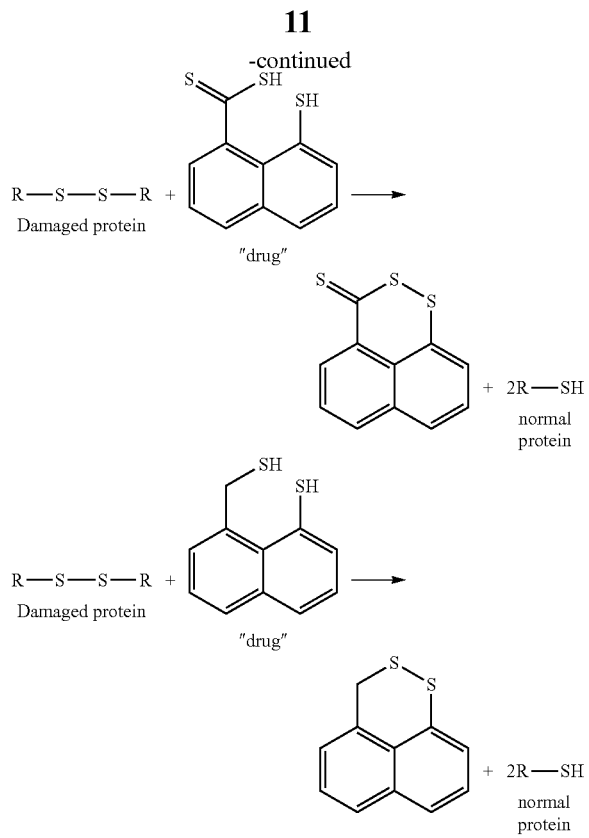

Antioxidant drugs should better Abe in their "reduced forms". When quenching free radicals, they are oxidized and become "oxidized forms". The "oxidized forms" are not active and have no more capability of quenching free radicals. Thiol and thiophenol are the "reduced forms" of antioxidant drugs, but are unstable for storage because they are prone to air oxidation. Hence, thiol and thiophenol must be chemically protected by other functional groups in order for a drug to be stored under atmosphere. At this point, the protected one is a prodrug that can release the drug as active "reduced form" in vivo where the protection group is chemically disconnected. The protection groups selected in this invention also act as penetration enhancer in order for a drug to be better delivered. In addition, the protection groups must have no toxicity issue.

As a summary, each novel molecule in this invention consists of at least two thiol groups. When oxidized, the sterical configuration allows them to form a 5 or 6-membered ring with a new disulfide bond in the ring. The thiol group is covalently single-bonded with a carbon atom located on aromatic ring, at benzylic position of aromatic ring, or at allylic position. In chemistry theory, thiophenol is stronger antioxidant than alkyl thiol. Based on these rules for design, there are 12 basic categories (A-L) of novel dithiol-containing antioxidants, as shown in FIG. 1 of drawings.

The variable part is the matrix that can be either regular aromatic ring or aromatic heterocyclic ring, with any possible combinations. Therefore, a large variety of new compounds are designed, with consideration of drug delivery that usually requires drug compounds to be amphipathic. Functional groups that are covalently bonded with thiols act as not only protection group, but also penetration enhancer for drug delivery. These functional groups include, but not limited to, amino acid, vitamin B's, choline, dopamine, EDTA, carbohydrate, nucleic base, citric acid, succinic acid, heterocycles, etc. The novel, drug-to-be molecules are numbered in Arabic hereafter unless otherwise notified.

Figure 2:
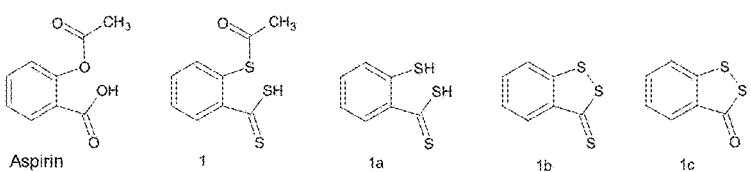
FIG. 2 illustrates some novel aspirin mimics.
Figure 3:
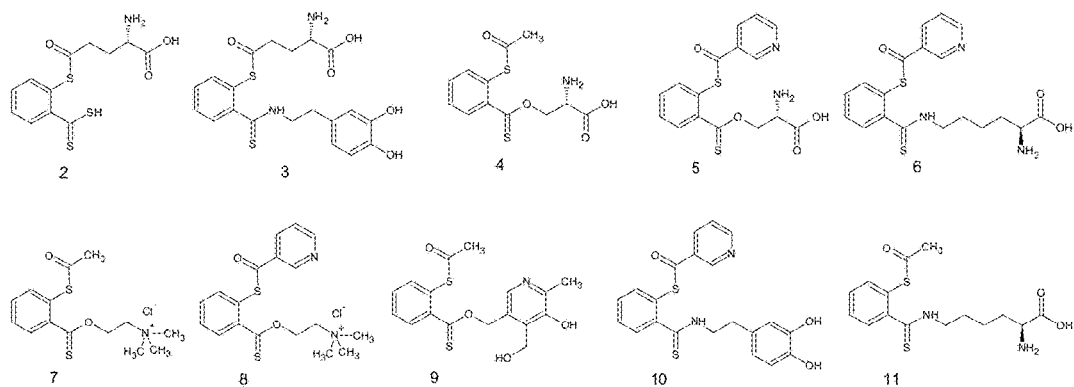
FIG. 3 illustrates novel aspirin mimics with different protection groups.
Figure 4:
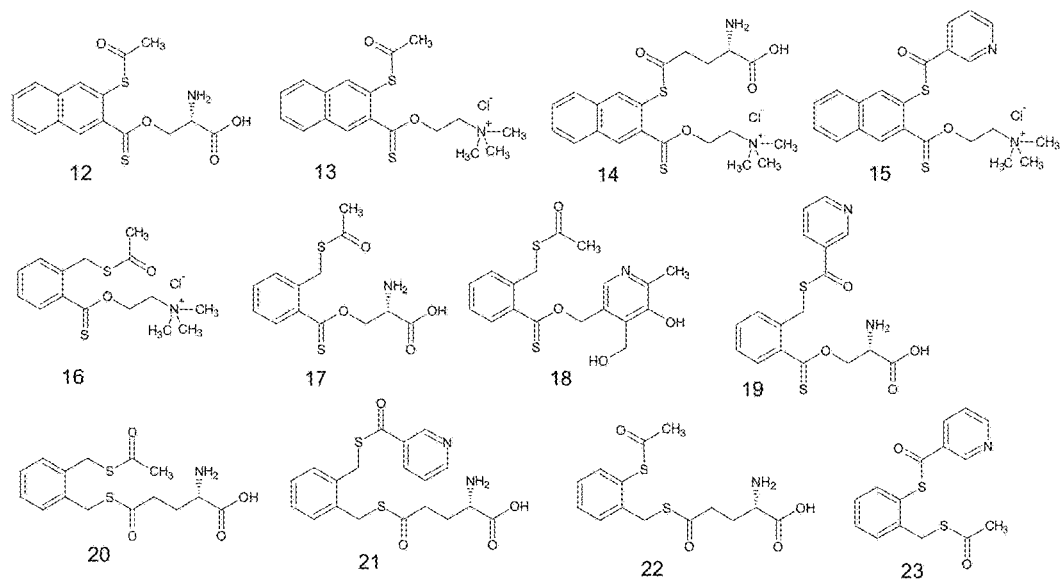
FIG. 4 illustrates novel aspirin mimics with some extended structure alteration.

Aspirin is probably the most popular drug in history. It is widely used in many indications as pain-killer, anti-inflammation, fever-reducer, preventing stroke and heart attack, etc. Expanded applications of aspirin in treatment and/or prevention of Alzheimer's disease, cancer and diabetes are under wide studies in recent years. Compound 1 is the mimic of aspirin (FIG. 2 of drawings), as a drug candidate in this invention. Compound 1a, the mimic of salicylic acid, would be the active form of compound 1 in vivo. As 1c is a known compound, compound 1b would reasonably be the oxidized form of compound 1a. Therefore, compound 1, as a new chemical entity and pro-drug of novel antioxidant, would be promising to beat aspirin in many indications With different protection groups, more drug-to-be molecules of aspirin mimics are depicted (FIG. 3 of drawings). After disconnection of protection group in vivo and being oxidized when quenching free radicals, compounds 3-11 would offer compound 1c as the oxidized form in common. There are more examples of aspirin mimics with extended structure alteration (FIG. 4 of drawings).

Figure 5:
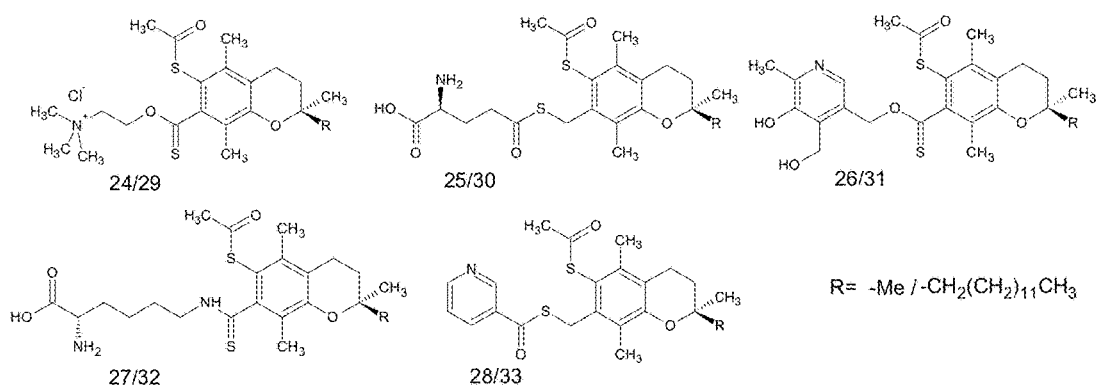
FIG. 5 illustrates novel vitamin E mimics with different protection groups.
Figure 6:
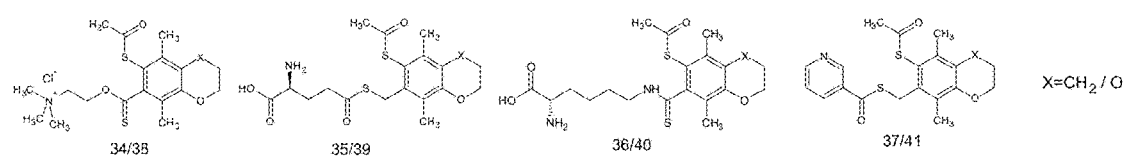
FIG. 6 illustrates novel vitamin E mimics with some extended structure alteration.

Vitamin E is a naturally occurring antioxidant and served as an important dietary nutrition. Vitamin E family has two groups: tocopherols and tocotrienols. Each group has four forms: alpha (α), beta (β), gamma (γ), and delta (δ). The capability of vitamin E as antioxidant and free radical scavenger is inferior to that of novel drug molecules in this invention. Besides, its bioavailability is poor due to low solubility in water. Some novel designs of vitamin E mimics rare depicted (FIG. 5 of drawings). There are more novel molecules of vitamin E mimics with extended structure alteration (FIG. 6 of drawings).

Figure 7:
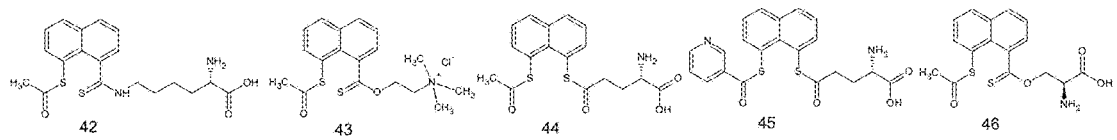
FIG. 7 illustrates novel drug molecules on the naphthalene matrix.

1,8-Dithionaphthalene represents a class of most powerful scavengers for free radicals in this invention, as both thiols are thiophenol-like and it forms a 5-membered ring when oxidized. Novel drug molecules on skeleton of 1,8-dithionaphthalene with different protection groups are depicted (FIG. 7 of drawings).

Figure 8:
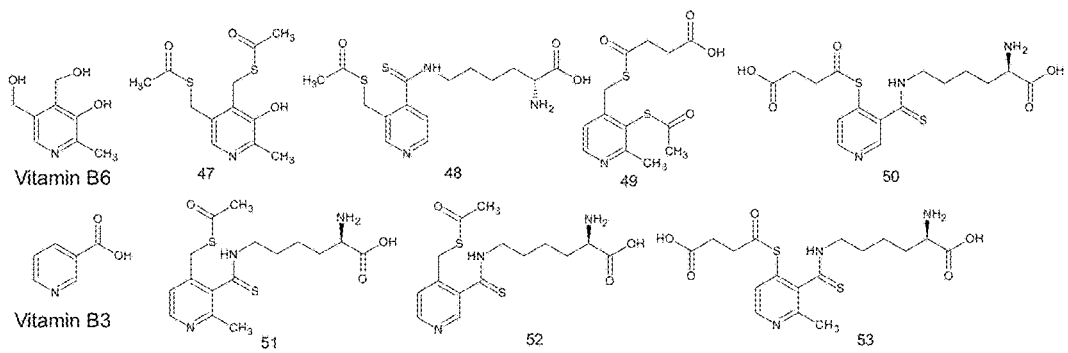
FIG. 8 illustrates novel mimics of pyridoxine and niacin with some extended structure alteration.
Figure 9:
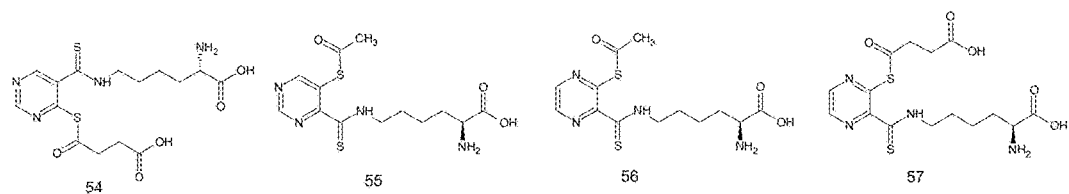
FIG. 9 illustrates some novel molecules on the pyrimidine or pyrazine matrix.

Vitamin B6 (pyridoxine) and vitamin B3 (niacin) are water-soluble vitamins. Both play essential roles in many important metabolic processes. Some novel designs of their mimics with different protection groups are depicted (FIG. 8 of drawings). They are similar to those molecules in FIG. 3 and FIG. 4 of drawings. Instead of benzene matrix, these are on pyridine matrix. Some novel molecules on pyrimidine or pyrazine matrix are also depicted (FIG. 9 of drawings).

Figure 10:
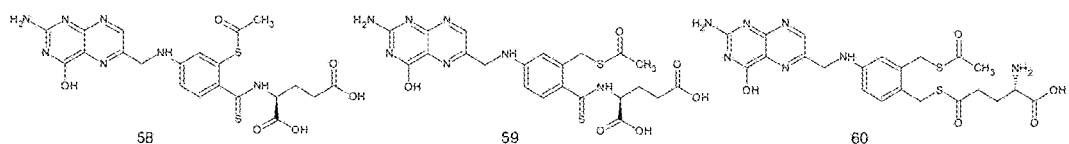
FIG. 10 illustrates novel folic acid (vitamin B9) mimics with some extended structure alteration.

Folic acid (vitamin B9) is an important nutrition for embryo development. In the case of cancer indication, cancer cells need high amount of folic acid for high growth rate. This may shed light for folic acid mimics to selectively deliver drug to cancer cells. Some novel molecules of folic acid mimics are depicted (FIG. 10 of drawings).

Figure 11:
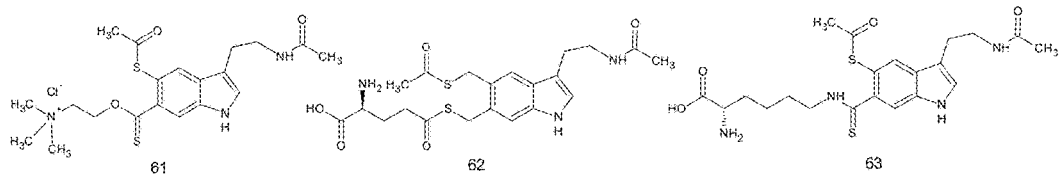
FIG. 11 illustrates novel melatonin mimics with some extended structure alteration.

Melatonin is a hormone secreted by the pineal gland in the brain. It helps regulate sleep-wake cycle. It is also served as antioxidant according to some publications. Some novel molecules of melatonin mimics are depicted (FIG. 11 of drawings).

Figure 12:
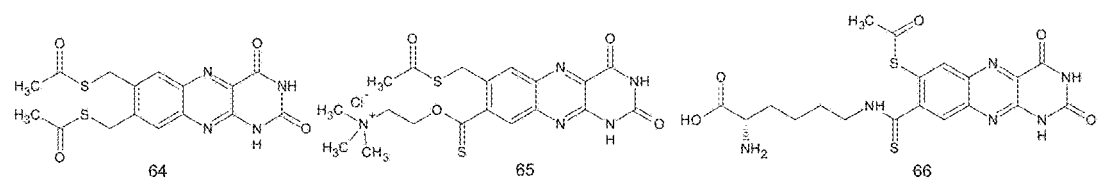
FIG. 12 illustrates novel riboflavin (vitamin B2) mimics with some extended structure alteration.

Riboflavin (vitamin B2) is a water-soluble vitamin and is required for many cellular processes. Some novel molecules of its mimics are depicted (FIG. 12 of drawings). The heterocyclic part of riboflavin is retained for the sake of drug delivery.

Figure 13:
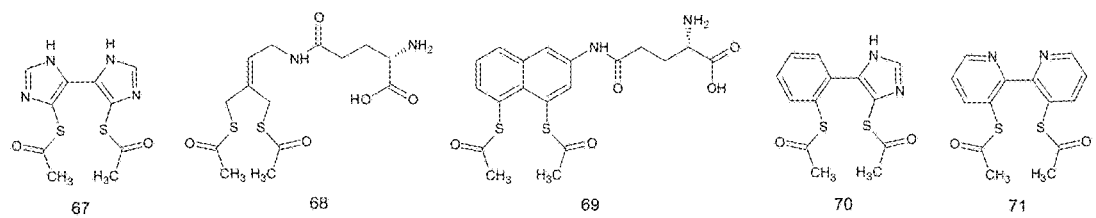
FIG. 13 illustrates some novel molecules with other matrices.
Figure 14:
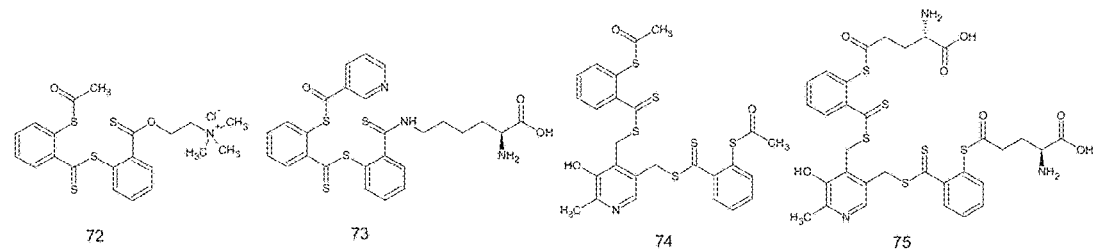
FIG. 14 illustrates some novel molecules with "dimer" or "trimer" of the antioxidants.

For each of basic styles in FIG. 1 of drawings, numerous molecules can be drawn. For a flavor of that, several novel compounds are depicted (FIG. 13 and FIG. 14 of drawings). The mimics of some naturally occurring products outlined above can certainly play a key role in this invention. Molecular structure optimization of the numbered compounds can be made based on the data feedback from their pre-clinical tests, such as efficacy, ADME, DMPK, etc. Good drug candidates will be moved forward to clinical trial and beyond.

2. Uses of the Novel Antioxidants in Treatment and/or Prevention of Major Diseases Free radical oxidation has been reported to associate with following indications, Alzheimer's disease, Parkinson's disease, diabetes, cardiovascular disease, cancer, renal disease, hypertension, hypercholesterolemia, hyperlipidemia, rheumatoid arthritis, pain, inflammation, stroke, HIV, aging, acne, cataract, age-related macular degeneration, glaucoma, etc. The potential application of novel drug molecules in this invention could be applied to treatment and/or prevention of these indications.

Age-related cataract is cloudiness of lens that consists of proteins and water. The proteins in lens are transparent in normal array. When oxidized by free radicals, the lens proteins become cross-linked by forming disulfide bonds, leading to structure change of the proteins and distortion of protein array in lens, and resulting in permanent cloudiness. Currently, there is no medication available to cure cataract. Surgical removal of opaque lens and implanting artificial lens is the only therapy for cataract patients. Surgery therapy is simple, but relatively costly.

According to thiol-disulfide exchange in scheme IV and scheme V, oxidative damage of lens protein could be reversed to normal lens protein. Thus, novel drug molecules in this invention as the highest powerful scavengers of free radicals could have highly promising therapeutic effects in both treatment and prevention of age-related cataract. The cornea barrier is a challenger for drug delivery of eye drop medication. This issue would be addressed by several novel drug molecules in this invention designed as amphipathic compounds.

Alzheimer's disease is caused by sclerosis of beta-amyloid (peptide) and/or fibrosis of tau protein in the brain. Free radical oxidation is a prime suspect for these protein tangles. There is currently no therapy for Alzheimer's disease. Therefore, there is an urgently need to have a drug to prevent this disease, to stop the progress of this disease, or even to cure this disease.

Since sclerosis of beta-amyloid (peptide) or fibrosis of tau protein in the brain is highly ascribed to free radical, oxidation, novel drug molecules in this invention possessing the highest powerful scavengers of free radicals could have promising therapeutic effects in both treatment and prevention of Alzheimer's disease. Blood-brain barrier is a challenger for drug delivery of brain medication. This issue would be addressed by several novel drug molecules in this invention designed with moiety of choline, dopamine, amino acids, etc. Similar applications could be for Parkinson's disease and other neurodegenerative diseases associated with oxidative stress.

Low density lipoprotein (LDL) is prone to free radical oxidation on its lipid part. The oxidized LDL can become plaques and hard to remove, leading to narrower blood vessel, causing ischemic stroke and cardiovascular diseases. The oxidized lipids are the suspected causes of inflammation. The novel drug molecules in this invention possessing the highest powerful scavengers of free radicals would find applications in prevention and/or treatment of rheumatoid arthritis, ischemic stroke and relevant cardiovascular diseases, such as atherosclerosis, hyperlipidemia, heart attack, etc.

Oxidative stress has been associated with many cancers. The uses of antioxidants in prevention and/or treatment of cancers have been widely studied and published. But, there is still no major breakthrough yet. Some novel antioxidant molecules in this invention, especially novel molecules of folic acid mimics, would find applications in prevention and/or treatment of cancers, such as liver cancer, lung cancer, pancreatic cancer, stomach cancer, breast cancer, prostate cancer, colon cancer, etc.

3. Chemical Synthesis of the Novel Antioxidant Molecules in this Invention

Chemical transformations of relevant functional groups have been well reported from reliable sources such as JACS and Organic Synthesis. Several typical chemical conversions are shown in scheme VI. Therefore, rational designs for synthetic routes of new chemical entities in this invention are considered as highly feasible.

Scheme VI. Reported Chemical Transformation

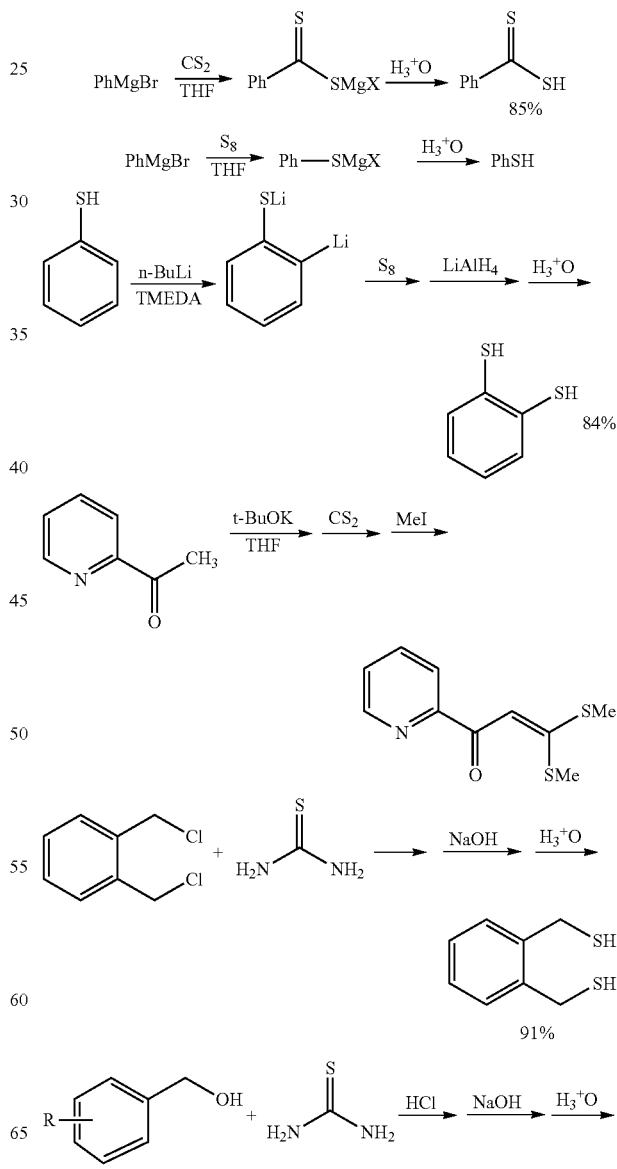

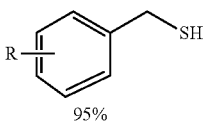

Examples of chemical synthesis of novel antioxidants in this invention are given below. Typical synthetic routes of novel compounds 1 and 74 in this invention have been shown in scheme VII.

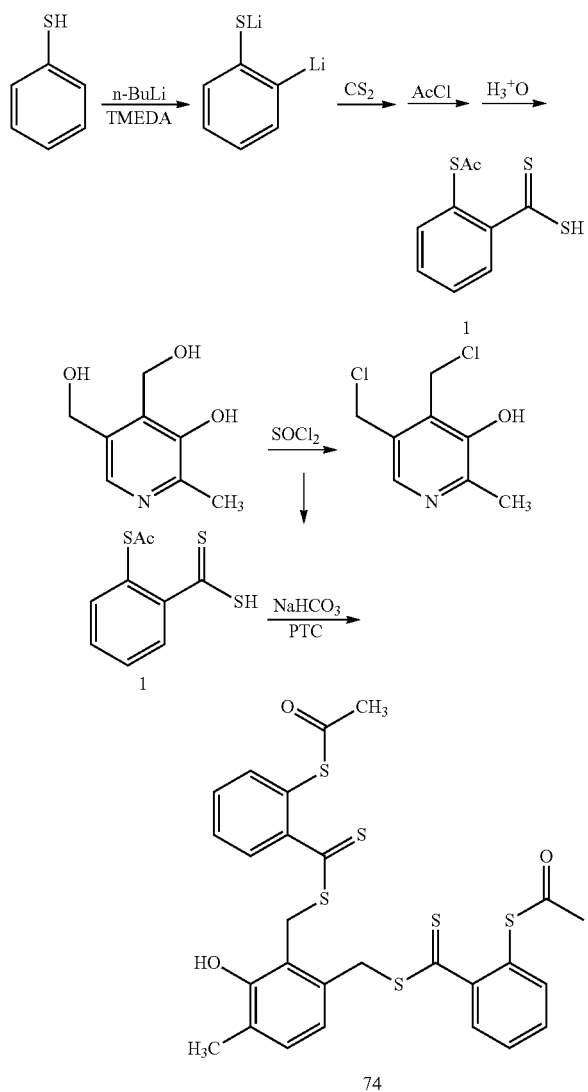

Starting material thiophenol is commercially available, which can also be synthesized from bromobenzene via Grignard reaction as reported. Lithiation of thiophenol gives ortho-directed lithiation intermediate. The lithiated intermediate reacts with carbon disulfide, followed by acetylation to afford compound 1. Pyridoxine (vitamin B6) treated with thionyl chloride could give di-chloride intermediate as shown in scheme VII. The di-chloride intermediate could efficiently react with compound 1 to afford compound 74 in the presence of sodium bicarbonate and phase transfer catalyst (PTC) such as tetrabutylammonium bromide (TBAB).

What is claimed is:

1. A compound comprising at least one pair of functional groups that consist of one functional group as thiol (—SH), optionally acylated, and another one as either carbodithioic acid (—CSSH) or carbothioic acid (—COSH), which when oxidized can form an intramolecular 5 or 6-membered ring via a disulfide bond, wherein said one pair functional groups are each optionally protected by an independently selected protecting group that is removable under physiological conditions for the purpose of drug delivery.

2. The compound of claim 1, wherein each of the pair of functional groups is covalently single-bonded with a carbon atom located on an aromatic ring that is selected from the group consisting of benzene, diphenylene, naphthalene, phenanthrene, anthracene, aromatic heterocyclic rings and combinations thereof.

3. The compound of claim 1, wherein each of the pair of functional groups is optionally protected by forming a covalent bond with another functional group or molecular moiety independently selected from the group consisting of acetyl (—Ac), succinic acid, amino acid, vitamin B's, choline, dopamine, EDTA, carbohydrate, nucleic base, citric acid, and heterocycles for the purpose of drug delivery in vivo and drug storage.

4. The compound of claim 1, further comprising one or more other moieties that are independently selected from the group consisting of carbohydrate, nucleic base, amino acid, citric acid, EDTA, and building blocks of vitamins, as a penetration enhancer to increase bioavailability.

5. The compound of claim 1, wherein the compound is synthesized by means of synthetic organic chemistry.

6. A pharmaceutical or dietary supplement composition comprising a compound of claim 1 and a pharmaceutically acceptable carrier.

7. The pharmaceutical or dietary supplement composition of claim 6, wherein the compound is selected from the group consisting of:

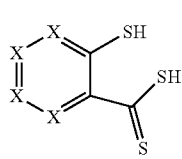

A

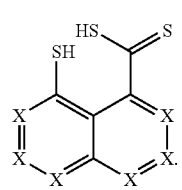

B

X = CH, N

8. The pharmaceutical or dietary supplement composition of claim 6, wherein the compound is selected from the group consisting of:

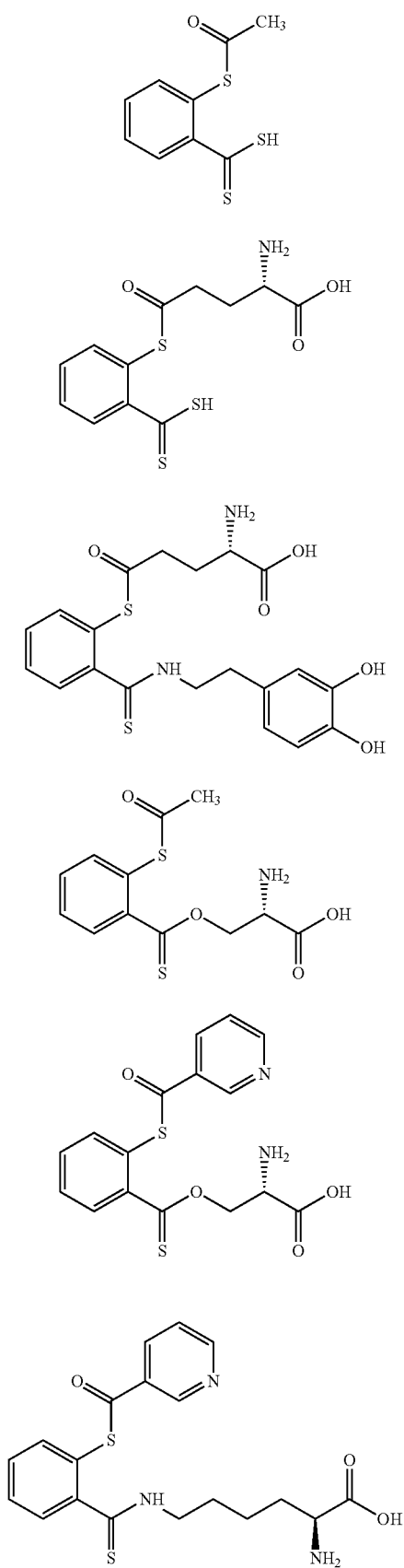
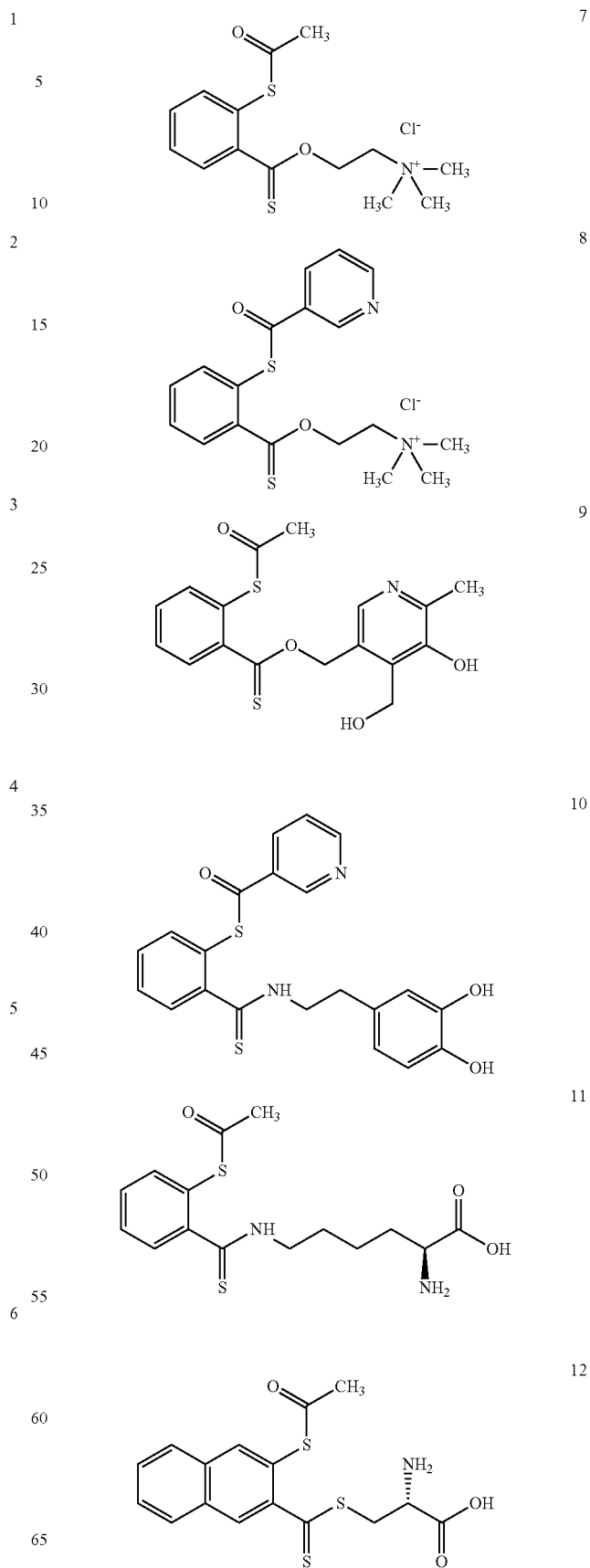

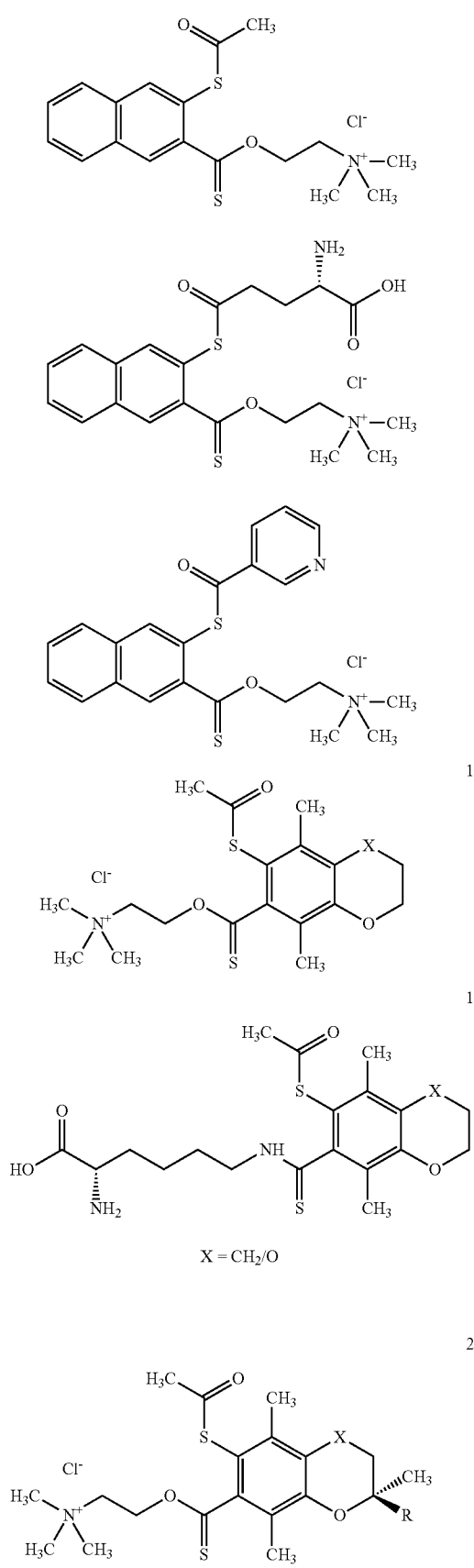

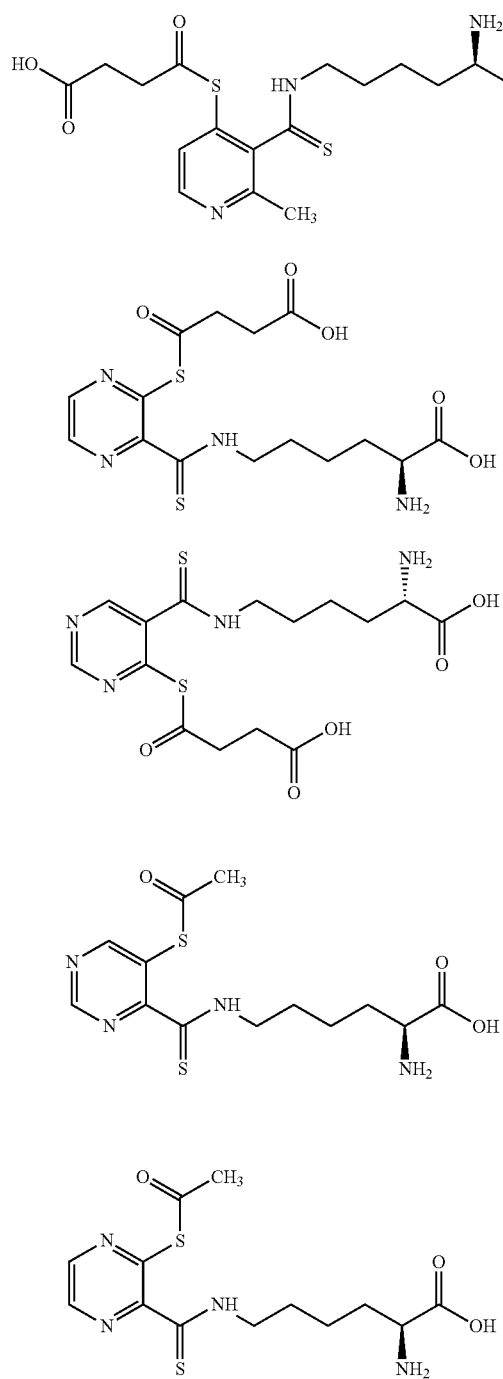
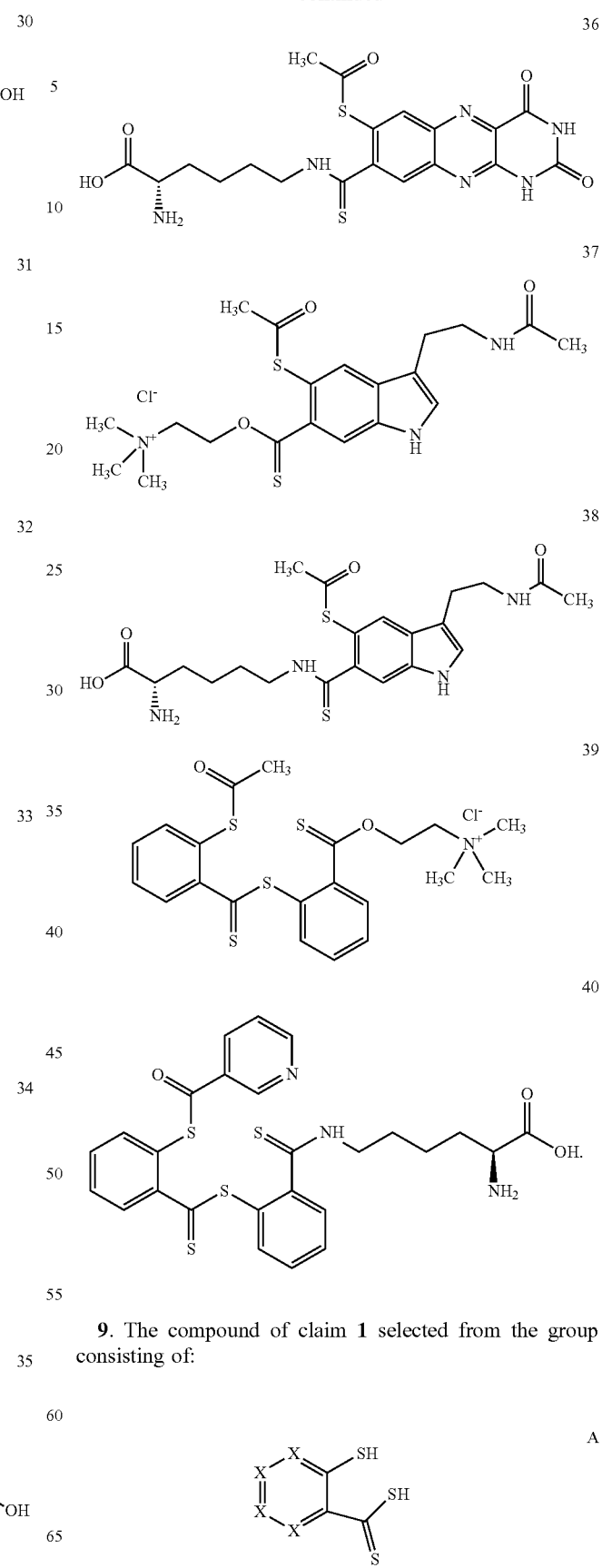
9. The compound of claim 1 selected from the group consisting of:
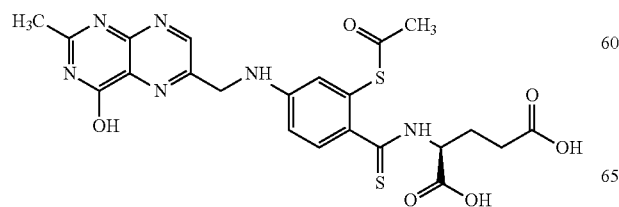

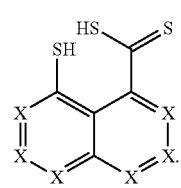
X = CH, N
10. The compound of claim 1 selected from the group consisting of:
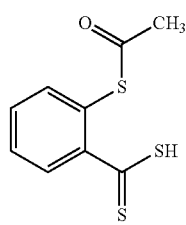
1
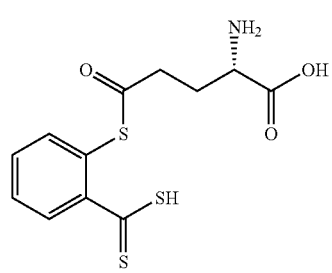
2
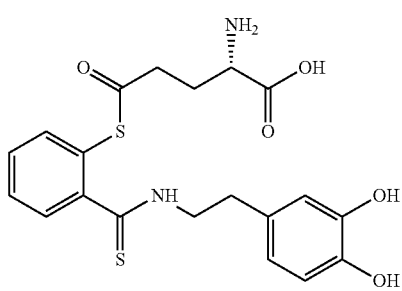
3
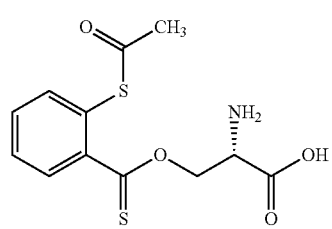
4
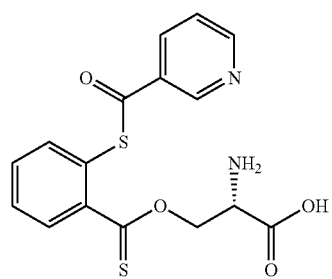
5
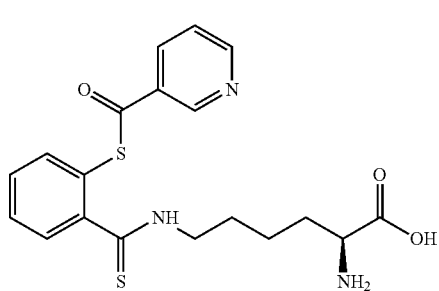
6
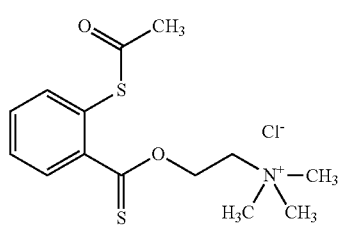
7
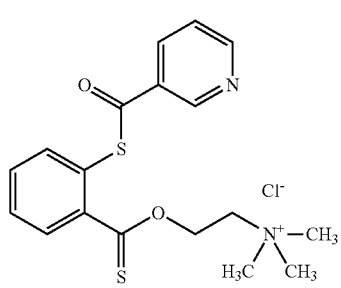
8
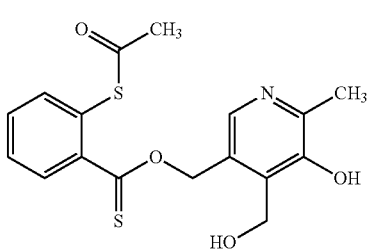
9
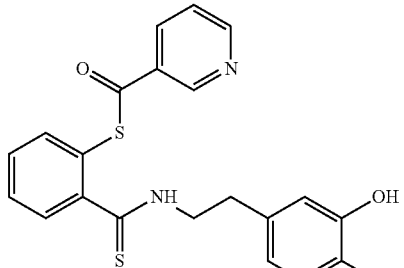
10
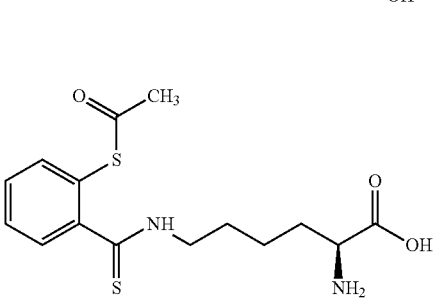
11

-continued

12

13

14

15

16/17

18/19

X = CH₂/O

-continued

20/21

22/23

24/25

R = —Me/ —CH₂(CH₂)₁₁CH₃

26

27

28

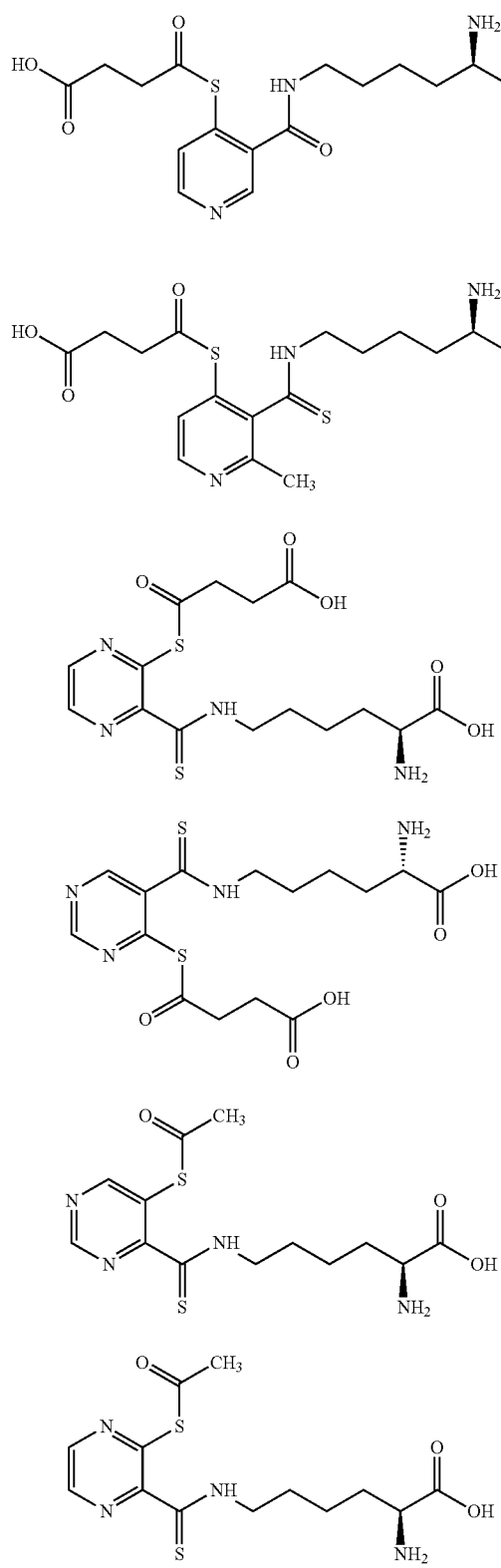
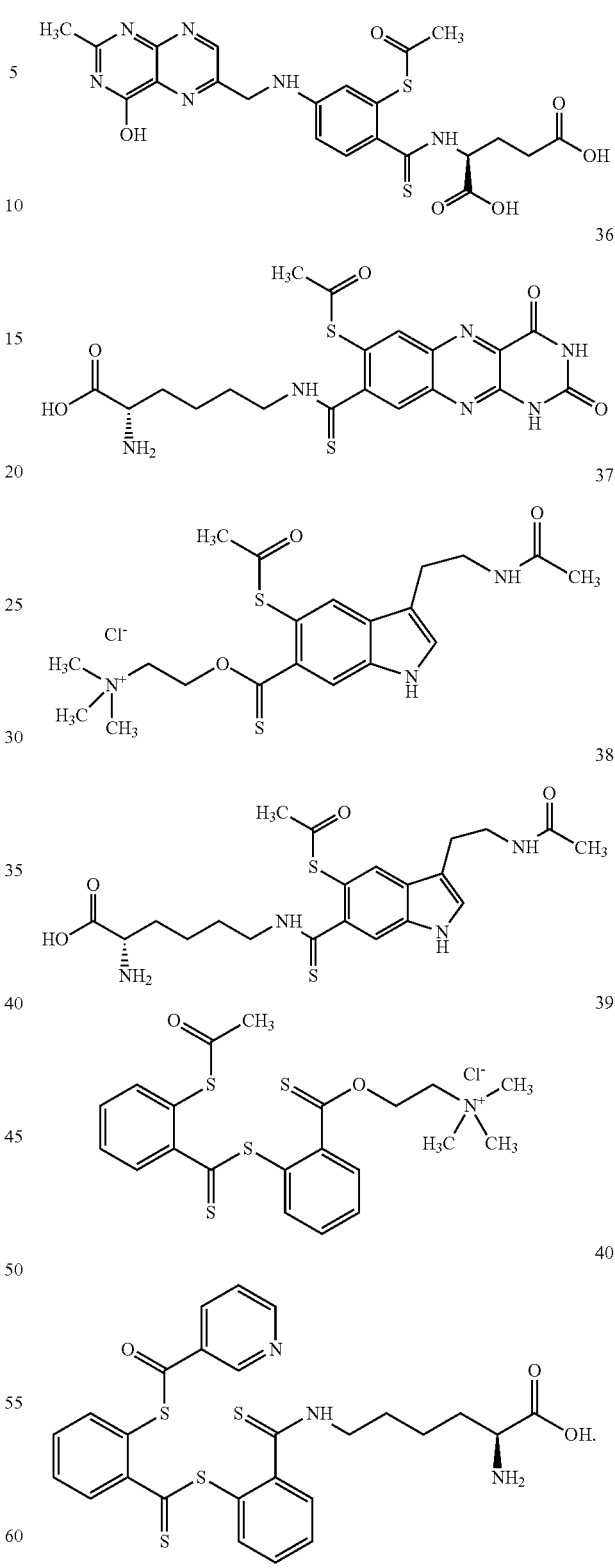
* * * * *